United States Patent
Diedering et al.

(12)

(10) Patent No.: US 11,452,628 B2
(45) Date of Patent: Sep. 27, 2022

(54) LOADING SYSTEMS FOR COLLAPSIBLE PROSTHETIC HEART VALVE DEVICES AND METHODS THEREOF

(71) Applicant: 4C Medical Technologies, Inc., Maple Grove, MN (US)

(72) Inventors: Jason S. Diedering, Minneapolis, MN (US); Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 151 days.

(21) Appl. No.: 16/848,328

(22) Filed: Apr. 14, 2020

(65) Prior Publication Data

US 2020/0323668 A1 Oct. 15, 2020

Related U.S. Application Data

(60) Provisional application No. 62/833,862, filed on Apr. 15, 2019.

(51) Int. Cl.
*A61F 2/95* (2013.01)
*A61F 2/24* (2006.01)

(52) U.S. Cl.
CPC ............ *A61F 2/9525* (2020.05); *A61F 2/243* (2013.01); *A61F 2/2436* (2013.01); *A61F 2/2439* (2013.01)

(58) Field of Classification Search
None
See application file for complete search history.

(56) References Cited

U.S. PATENT DOCUMENTS

| | | | |
|---|---|---|---|
| 4,424,833 A | 1/1984 | Spector et al. | |
| 2007/0239271 A1 | 10/2007 | Nguyen | |
| 2008/0281398 A1* | 11/2008 | Koss | A61F 2/966 623/1.12 |
| 2009/0076585 A1 | 3/2009 | Hendriksen et al. | |
| 2010/0256749 A1 | 10/2010 | Tran et al. | |
| 2011/0046712 A1* | 2/2011 | Melsheimer | A61F 2/844 623/1.11 |

(Continued)

FOREIGN PATENT DOCUMENTS

WO 2017/194504 11/2017

OTHER PUBLICATIONS

International Search Report and Written Opinion issued in related PCT/US2020/028240, dated Jul. 20, 2020.

(Continued)

*Primary Examiner* — Shaun L David
(74) *Attorney, Agent, or Firm* — Weiss & Arons LLP (57) ABSTRACT

Loading systems for prosthetic heart valve devices are disclosed. A loading funnel is provided within a watertight interior space that is at least partially filled or fillable with biocompatible fluid. Funnel may have a cylindrical end to which is connected a delivery catheter having a lumen that will receive the collapsed prosthetic heart valve device. An expanded prosthetic heart valve device may be placed within the funnel and pushed or pulled into the funnel which provides a predictable, reliable and repeatable surface for collapsing the prosthetic heart valve device. Ultimately the prosthetic heart valve device is collapsed and translated into the lumen of the delivery catheter for further translation therealong and release into the heart chamber of interest.

4 Claims, 9 Drawing Sheets

(56) References Cited

U.S. PATENT DOCUMENTS

2011/0319988 A1* 12/2011 Schankereli .......... A61F 2/2436
623/2.11
2014/0277403 A1* 9/2014 Peter ..................... A61F 2/2418
623/2.11
2016/0220363 A1 8/2016 Peter

OTHER PUBLICATIONS

Notification Concerning Transmittal of International Preliminary Reprot on Patentability and International Preliminary Report on Patentability issued in related application PCT/US2020/028240, dated Oct. 28, 2021.

* cited by examiner

Open flush unit (105)  
FIG. 6A

Connect stent and delivery tools through opening (103)  
FIG. 6B

Fill bag with saline to flush and remove bubbles  
FIG. 6C

Pull stent into catherter via funnel  
FIG. 6D

Remove catheter from base of funnel  
FIG. 6E

Insert catheter into base of funnel-penetrating sealing membrane

FIG. 9A

Attach stent to catheter tip

FIG. 9B

Twist to secure top to funnel base

FIG. 9C

Fill reservoir with saline

FIG. 9D

Pull stent into catheter via funnel and pull wire

FIG. 9E

Remove catheter from base of funnel

LOADING SYSTEMS FOR COLLAPSIBLE PROSTHETIC HEART VALVE DEVICES AND METHODS THEREOF

CROSS-REFERENCE TO RELATED APPLICATIONS

This application claims the benefit of U.S. Provisional Application Ser. No. 62/833,862, filed Apr. 15, 2019 and entitled LOADING SYSTEMS FOR COLLAPSIBLE PROSTHETIC HEART VALVE DEVICES AND METHODS THEREOF, the entire contents of which are hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to devices, systems and features for loading of stents including but not limited to prosthetic heart valve devices into delivery catheters.

Description of the Related Art

Figure 1:
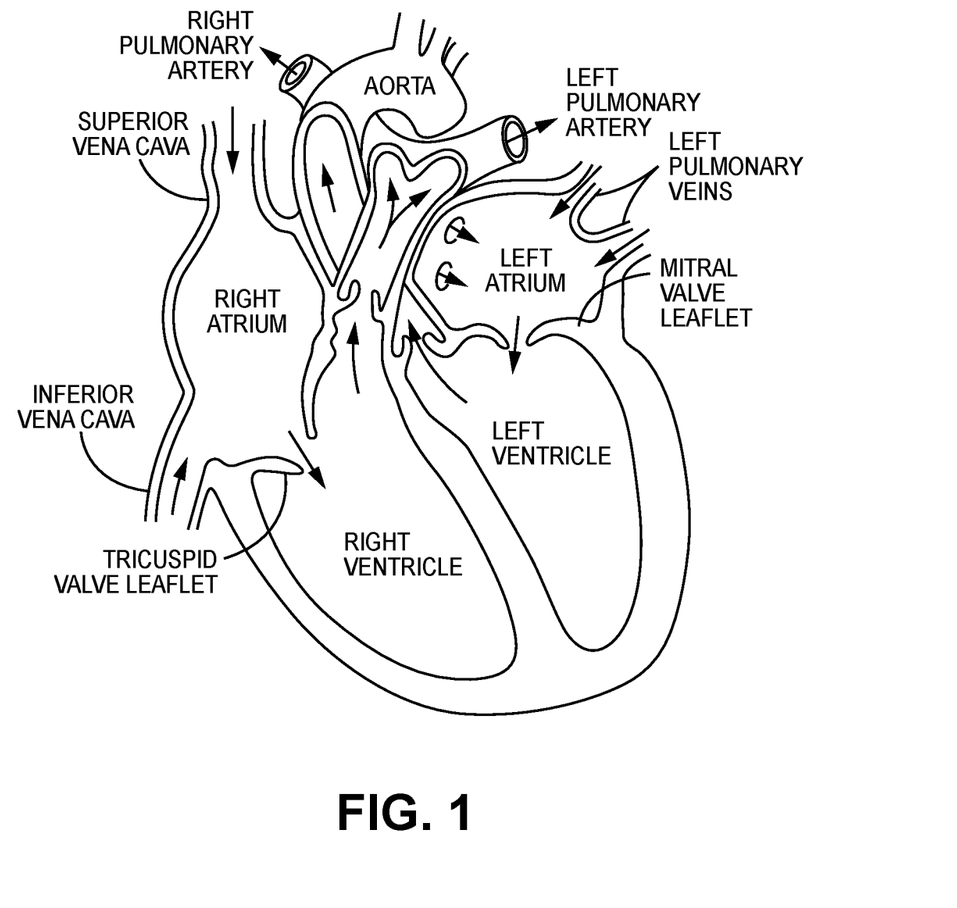
FIG. 1 illustrates certain features of the heart in cross-section.

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

Figure 2:
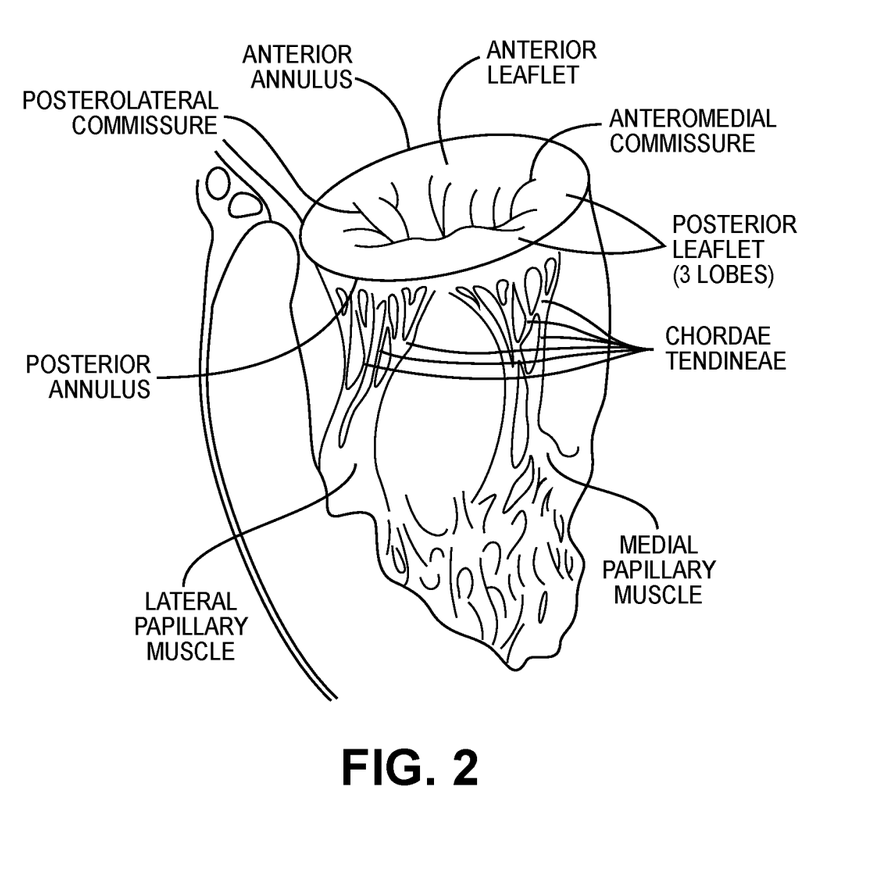
FIG. 2 illustrates a cross-sectional perspective view of the left side of the heart.

FIG. 2 illustrates the relationship between the left atrium, annulus, chordae tendineae and the left ventricle relative to the mitral valve leaflets. As is shown, the upper surface of the annulus forms at least a portion of the floor or lower surface of the left atrial chamber, so that for purposes of description herein, the upper surface of the annulus is defined as marking the lower boundary of the left atrial chamber.

Figure 3:
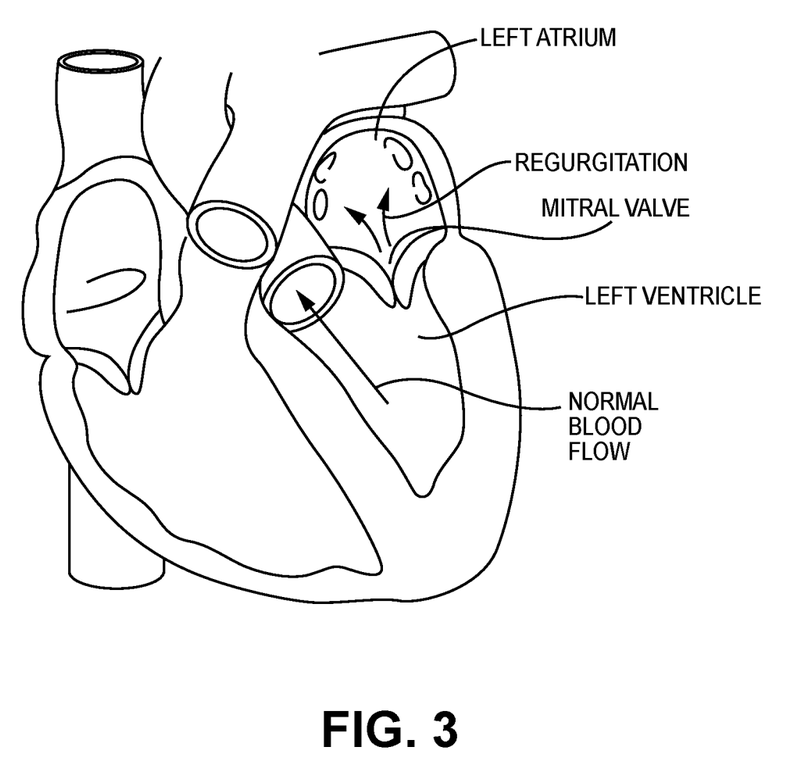
FIG. 3 illustrates a cross-sectional view of the heart showing retrograde blood flow resulting from mitral valve regurgitation compared with normal blood flow.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure. FIG. 3 illustrates regurgitant blood flow with an exemplary dysfunctional mitral valve.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat.

No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, all known prosthetic heart valves are intended for full replacement of the native heart valve. Therefore, these replacement heart valves, and/or anchoring or tethering structures, physically extend out of the left atrial chamber, in the case of mitral valves, and engage the inner annulus and/or valve leaflets, in many cases pinning the native leaflets against the walls of the inner annulus, thereby permanently eliminating all remaining functionality of the native valve and making the patient completely reliant on the replacement valve. In other cases, the anchoring structures extend into the left ventricle and may anchor into the left ventricle wall tissue and/or the sub-annular surface at the top of the left ventricle. Others may comprise a presence in, or engagement with, a pulmonary artery.

Obviously, there will be cases when native valve has lost virtually complete functionality before the interventional implantation procedure. In this case the preferred solution will comprise an implant that does not extent outside of, e.g., the left atrium, and that functions to completely replace the native valve function. However, in many other cases, the native valve remains functional to an extent and may, or may not, continue to lose functionality after the implantation procedure. A preferred solution in this case comprises delivery and implantation of a valve device that will function both as a supplemental or augmentation valve without damaging the native leaflets in order to retain native valve leaflet functionality as long as present, while also being fully capable of replacing the native function of a valve that slowly loses most or all of its functionality post-implantation of the prosthetic valve.

Known delivery systems for prosthetic heart valve devices can be improved by at least reducing loading forces and minimizing air introduction into the system during loading of the prosthetic heart valve device into a delivery catheter for collapsed transport through the patient's vasculature through the delivery catheter lumen to the subject heart chamber, e.g., atrium or ventricle. Once the collapsed prosthetic heart valve device is translated distally out of the delivery catheter lumen, it may expand from the collapsed transport configuration to an expanded working configuration(s).

Various embodiments of the several inventions disclosed herein address these, inter alia, issues.

DETAILED DESCRIPTION OF THE INVENTION

Generally, various embodiments of the present invention are directed to devices and methods for optimizing loading of a prosthetic heart valve device comprising a collapsible and expandable frame, e.g., a stent or other collapsible and expandable device into a delivery catheter lumen. The embodiments described herein optimize delivery of a prosthetic heart valve device by (1) reducing loading forces during collapsing and translating through the delivery catheter lumen; and/or (2) by reducing, minimizing or eliminating air introduction into the system comprising the prosthetic heart valve device and/or the lumen of the delivery catheter.

Figure 4:
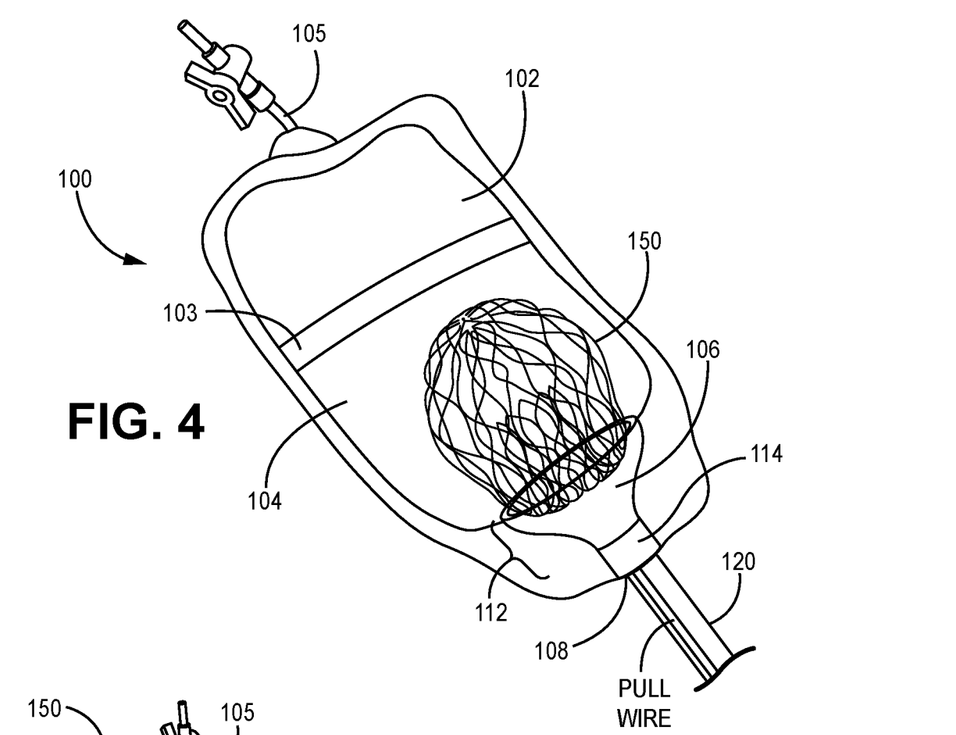
FIG. 4 illustrates a perspective view of one embodiment of the present invention.
Figure 5:
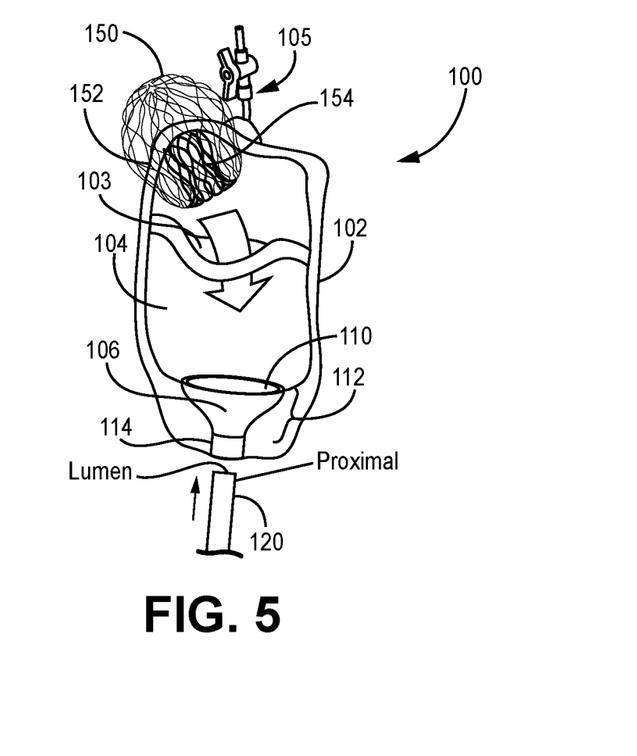
FIG. 5 illustrates a side view of one embodiment of the present invention.

FIGS. 4 and 5 illustrate one embodiment of the present invention comprising a container, e.g., a bag that may be sealable, at least partially filled with a biocompatible fluid such as saline or other fluid. FIG. 4 shows one embodiment of the basic structure while FIG. 5 provides a method 200 with method steps illustrated in combination with the structure of FIG. 4.

Thus, turning to FIGS. 4 and 5, one embodiment of a loading system 100 is illustrated. Loading system 100 comprises a resealable container 102, e.g., a bag, that is adapted to hold a biocompatible fluid 104 therein, e.g., saline within an interior defined by the container 102. Container may comprise a resealable opening 103 and a valved line or flush tube 105 to, inter alia, admit fluid into the container 102. A funnel 106 is disposed within the interior of the container, e.g., bag, 102 and immersed within the biocompatible fluid 104 held therein. Funnel 106, as known in the art, comprises an upper opening 110 that tapers down through a conical portion 112, terminating at a cylindrical portion 114 opposite the upper opening 114, wherein the upper opening 110 comprises a larger radius than the cylindrical portion 114.

The container 102 further comprises an access opening 108 into the interior of the container 102. This access opening 108 may be engaged by the distal cylindrical and/or conical tube portion(s) 110, 112 of the funnel 106, wherein the interconnection between the funnel 106 and the container 102 is generally sealed or at least partially water tight, to prevent fluid egress therefrom. Still more alternatively, the proximal end of a delivery catheter 120 may be disposed within the interior of the container 102, engaging the cylindrical portion 114 of funnel and immersed within the biocompatible fluid, wherein the interconnection between the proximal end of the delivery catheter 120 and the container 102 and/or funnel 106 is adapted to prevent substantial loss of fluid 104 when present.

Figures 7A, 7B:
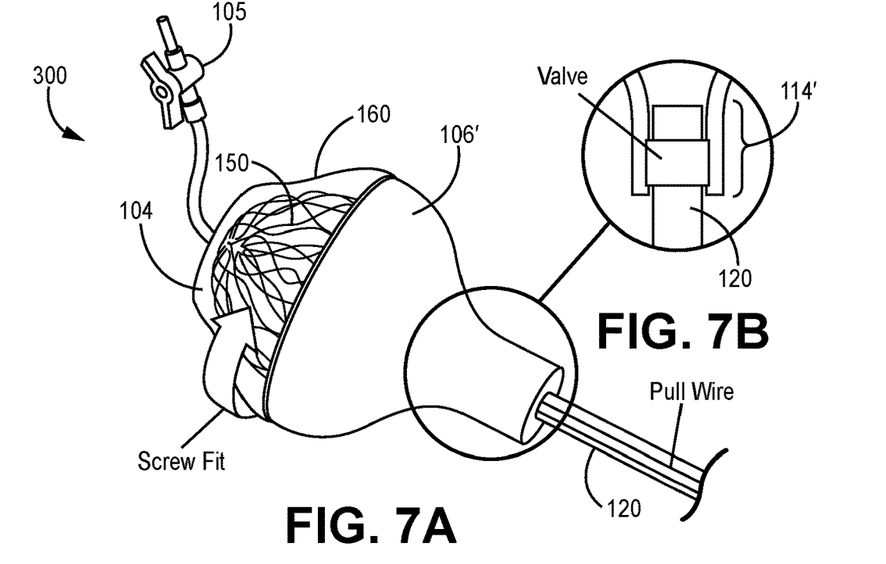
FIG. 7A illustrates a perspective view of one embodiment of the present invention.
FIG. 7B illustrates a cross-sectional view cutaway view of one embodiment of the present invention.
Figure 8:
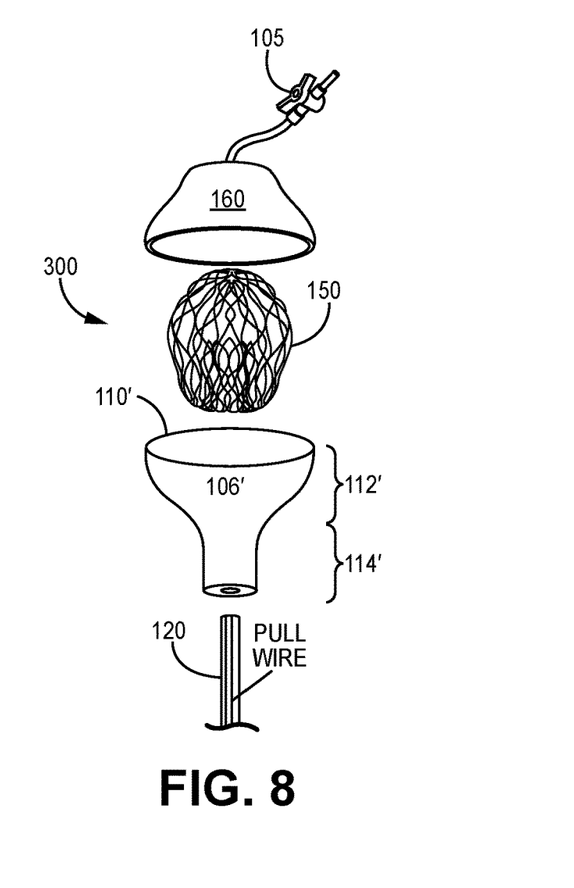
FIG. 8 illustrates an exploded view of one embodiment of the present invention.

Alternatively, the access opening 108 into the container's interior may comprise a self-sealing material that may be punctured by either the cylindrical portion 114 or conical portion 112 of the funnel 106 or by the proximal end of the catheter 120, but self-seals to prevent fluid loss after the puncture is achieved. A valve as shown in FIG. 7B may also be used.

Accordingly, either the cylindrical portion 114 or conical portion 112 of the funnel 106 may extend outwardly from the container 102 through an access opening 108, or the proximal end of the delivery catheter 120 may extend into the interior of the container 102 to connect with the cylindrical portion 114 of the funnel 106. What is required in any case is a fluid connection between the cylindrical portion 112 or conical portion 112 of the funnel 106 with the proximal end of the delivery catheter.

As shown, an expanded and collapsible prosthetic heart valve device 150 is placed into the container 102 through the resealable opening 103, placed into the fluid-filled interior of the container 102, positioned in the upper opening 110 of funnel 106 and pressed downward into the funnel's conical portion 112, thereby collapsing the heart valve device 150 in a manner that is repeatable and predictable with even distribution of loading forces around the collapsing frame 152, e.g., stent or equivalent as shown, of device 150. This prevents highly undesirable stressing of certain regions or elements of the frame 152 of the prosthetic heart valve device 150, including in the case of a stent, individual cells and/or struts comprising the outer collapsible frame 152.

As shown, in some embodiments an inner valve support 154, supporting prosthetic valve leaflets therein (leaflets not shown but as well-known to the skilled artisan) that is also a collapsible and expandable structure, may extend radially within the interior of the prosthetic heart valve device's outer frame 152. As shown, translation of the device 150 into the funnel also functions to collapse the inner valve support in a predictable, repeatable and evenly distributed loading force manner. Ultimately the device 150 is predictably and repeatably collapsed in a controlled manner until device 150 is loaded into the lumen of the delivery catheter 120 that is connected with container 102.

In addition to the reduction and/or evenly distributed, and predictably distributed, loading forces described above, this embodiment eliminates air introduction into the system, e.g., the prosthetic heart valve device 150 and the lumen of the delivery catheter, by immersion into the biocompatible fluid 104. Once immersed into the fluid 104, no air is present at the funnel 106, only fluid 104 and the collapsing device 150 may enter the delivery catheter lumen.

As shown, certain embodiments of the container 102 may comprise a bag that comprises a seal or resealable opening 103 midway along its length to provide a region that is completely filled with fluid 104 and within which the expanded device 150 is completely immersed. Tipping the container 102, or bag, upright so that the access opening 108 is at the bottom side results in any air rising to the top of the bag or container 102, with the fluid 104 and prosthetic heart valve device 150 being completely immersed. From there, controlled collapsing of the immersed heart valve device 150 as described above is achieved into the cylindrical portion 114 of the funnel 106 and then the fully collapsed device 150 may be translated distally into the lumen of the delivery catheter 120 toward the subject heart chamber.

The connection of the container 102 and/or funnel 106 with the delivery catheter 120 may remain in place during translation of the collapsed device 150 or the delivery catheter 120 may be disconnected from the container 102 and/or funnel 106 after collapsed translation of the device 150 into the lumen of the delivery catheter 120.

Figure 6A:
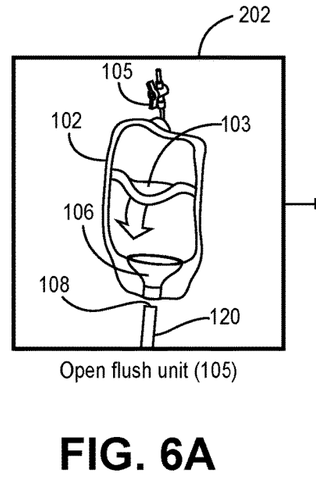
FIG. 6A illustrates an exemplary method step for loading a collapsible prosthetic heart valve device into the lumen of a delivery catheter according to embodiments of the present invention.

FIGS. 6A-6E provide illustration of one exemplary method using the embodiments described above. Thus, as shown in FIG. 6A at step 202, the container, in this case a bag, 102 is provided in an upright position, with the access opening 108 at the bottom of the container 102. A flush tube or line 105, in fluid connection with an external fluid reservoir (not shown), is connected and that allows controlled fluid 104 flow therethrough into the container's interior by, e.g., a stopcock as shown. Alternatively, the container 102 may simply be filled through the sealable opening 103.

Figure 6B:
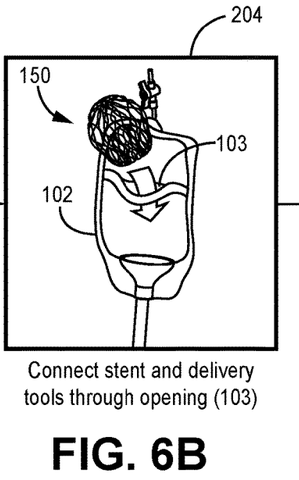
FIG. 6B illustrates an exemplary method step for loading a collapsible prosthetic heart valve device into the lumen of a delivery catheter according to embodiments of the present invention.
Figure 6C:
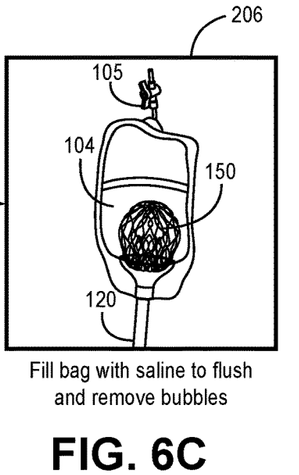
FIG. 6C illustrates an exemplary method step for loading a collapsible prosthetic heart valve device into the lumen of a delivery catheter according to embodiments of the present invention.

In FIG. 6B at step 204, the expanded prosthetic stent 150 and any related delivery tools, e.g., a push and/or pull wire(s) are introduced into the biocompatible fluid 104, e.g., through the sealable opening 103. The bag or container 102 may either be pre-filled with biocompatible fluid 104, e.g., saline, before introducing the expanded device 150 into the container 102 or may be filled with biocompatible fluid 104 after the device 150 is introduced into the container 102. FIG. 6C illustrates at step 206, introducing the device 150 into the container with subsequent filling of biocompatible fluid.

Figure 6D:
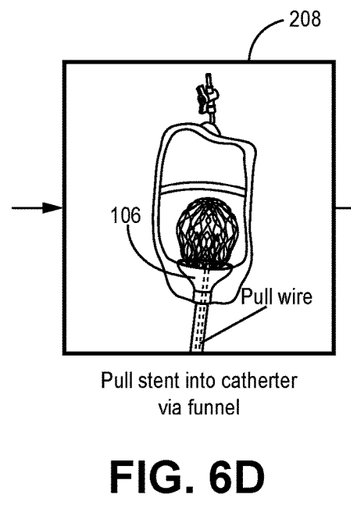
FIG. 6D illustrates an exemplary method step for loading a collapsible prosthetic heart valve device into the lumen of a delivery catheter according to embodiments of the present invention.

FIG. 6D at step 208 then shows the collapsing of the device 150 into the catheter lumen via the controlled collapsing through the funnel 106 structure as described above. The device 150 may be pulled from a distal end of the catheter lumen using a detachable wire (pull wire) connected to the prosthetic heart valve device 150 or may be pushed into the proximal end of lumen of the catheter 120. If a detachable pull wire is used, it may be detached and removed from the lumen of the catheter 120 when the collapsed prosthetic device 150 is loaded within the delivery catheter's lumen, or pull wire may be left in place.

Figure 6E:
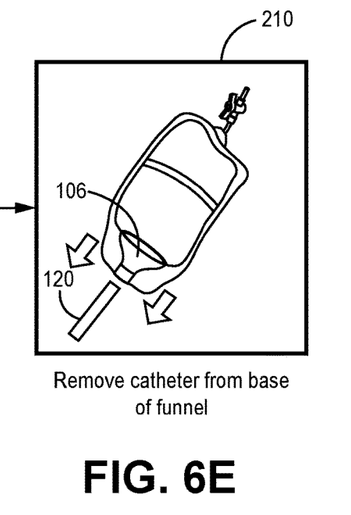
FIG. 6E illustrates an exemplary method step for loading a collapsible prosthetic heart valve device into the lumen of a delivery catheter according to embodiments of the present invention.

FIG. 6E shows step 210, the detachment of the container 120 and funnel 106 from the delivery catheter 120 after the collapsed device 150 is loaded within the delivery catheter 120.

Turning now to FIGS. 7A-9F, another embodiment for a loading system for a collapsible prosthetic heart valve device is provided. The basic functionality behind this device is similar to that discussed above in that a funnel-type device is used to provide evenly distributed loading forces with great predictability to the collapsing prosthetic heart valve device and wherein the collapsing is done while the prosthetic heart valve device is immersed in biocompatible fluid and wherein the collapsed device is loaded into the lumen of a delivery catheter.

Here, as shown in the Figures, the expanded prosthetic heart valve device 150 is placed into the funnel 106' and may be connected with a pull wire extending through the lumen of the delivery catheter 120 and extending from the proximal and distal ends of the delivery catheter 120 to allow engagement of the pull wire and the device 150 at a proximal end of the delivery catheter and enabling of a pulling force engagement at the distal end of the delivery catheter 120 to urge the device 150 into and through the lumen of the delivery catheter 120. A valve may be provided in the cylindrical portion 114' or conical portion 112' of the funnel 106' as seen in FIG. 7B to help ensure fluid sealing before and during the loading process.

Figure 9A:
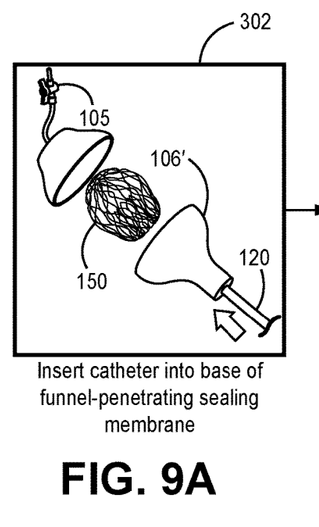
FIG. 9A illustrates an exemplary method step for loading a collapsible prosthetic heart valve device into the lumen of a delivery catheter according to embodiments of the present invention.
Figure 9B:
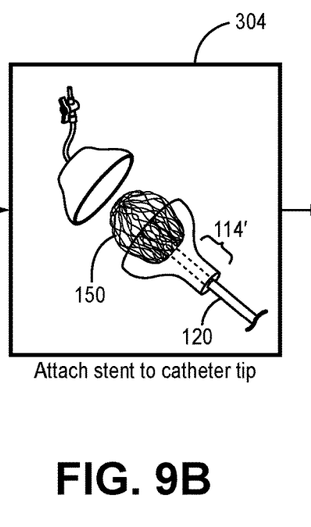
FIG. 9B illustrates an exemplary method step for loading a collapsible prosthetic heart valve device into the lumen of a delivery catheter according to embodiments of the present invention.

Also as shown, the proximal end of delivery catheter 120 may be attached or engaged with the cylindrical portion 114' or conical portion 112' of the funnel 106' to create a fluid communication between the funnel 106' and the lumen of the delivery catheter 120. These steps are shown in FIGS. 9A (step 302) and 9B (step 304).

Figure 9C:
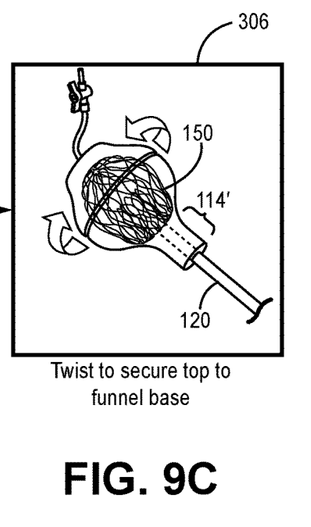
FIG. 9C illustrates an exemplary method step for loading a collapsible prosthetic heart valve device into the lumen of a delivery catheter according to embodiments of the present invention.

As shown in FIG. 9C and step 306, once the expanded prosthetic heart valve device 150 is placed in the funnel 106' as shown, a connecting top 160 is connected with, and covering, the upper opening 110' of the funnel 106 to create a substantially watertight interior. A fluid infusion line 105 may be in fluid communication with the substantially watertight interior as shown for infusing biocompatible fluid 104 such as saline into the interior to immerse the device 150 therein once the connecting top 160 is secured to the funnel 106'. The securement of the connecting top 160 to the upper opening 110' of the funnel 106' may be done by several known methods and mechanisms, including but not limited to screw threads.

Figure 9D:
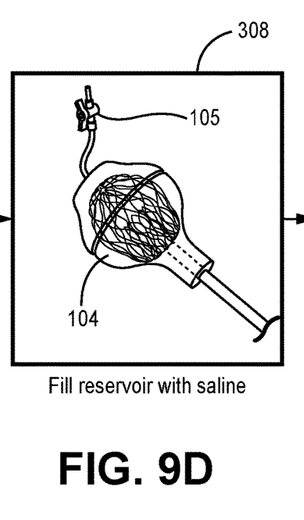
FIG. 9D illustrates an exemplary method step for loading a collapsible prosthetic heart valve device into the lumen of a delivery catheter according to embodiments of the present invention.

As shown in FIG. 9D and step 308, once the substantially watertight interior is defined and created, and at least partially filled with biocompatible fluid 104 via fluid supply line 105, a fluid communication is created between the watertight interior and the lumen of the delivery catheter 120.

Figure 9E:
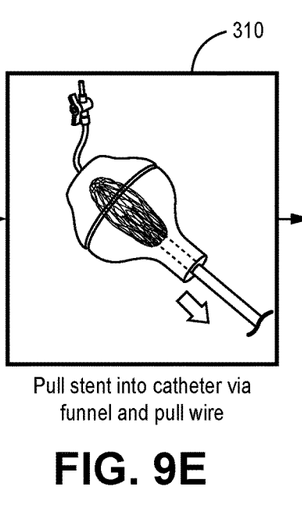
FIG. 9E illustrates an exemplary method step for loading a collapsible prosthetic heart valve device into the lumen of a delivery catheter according to embodiments of the present invention.
Figure 9F:
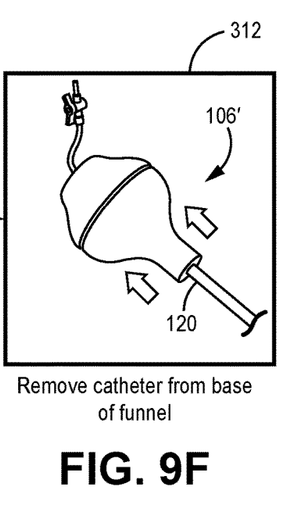
FIG. 9F illustrates an exemplary method step for loading a collapsible prosthetic heart valve device into the lumen of a delivery catheter according to embodiments of the present invention.

Now, as in FIG. 9E and step 310, the collapsing of the immersed prosthetic heart valve device 150 may be initiated by pulling distally on pull wire. Next, as in FIG. 9F and step 312, when the collapsed device 150 has reached a predetermined position within the lumen of the delivery catheter 120, the funnel 106' and catheter 120 may be disengaged or disconnected. Moreover, at that point pull wire may be disconnected and removed from the lumen of delivery catheter 120, or pull wire may remain attached.

Turning now to an alternate embodiment of a loading system as illustrated in FIGS. 10-12F. A funnel 106" is provided in detachable engagement or connection with a delivery catheter 120, wherein a fluid connection is created between the funnel 106" and the lumen of the delivery catheter 120. As in all previous embodiments, the lumen of the cylindrical or conical portion of the funnel 106" is substantially axially aligned with the lumen of the delivery catheter 120 when loading the prosthetic heart device 150 therein.

Figure 12A:
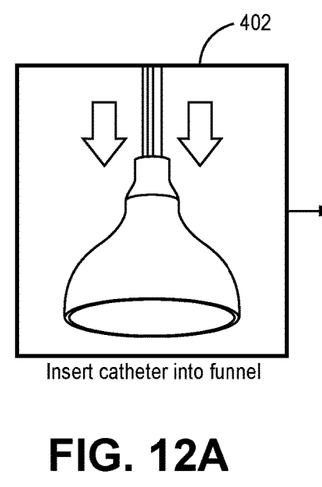
FIG. 12A illustrates an exemplary method step for loading a collapsible prosthetic heart valve device into the lumen of a delivery catheter according to embodiments of the present invention.
Figure 12B:
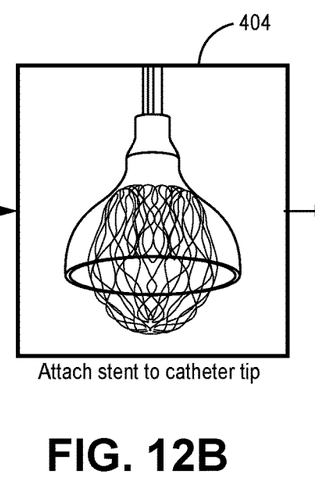
FIG. 12B illustrates an exemplary method step for loading a collapsible prosthetic heart valve device into the lumen of a delivery catheter according to embodiments of the present invention.

In this embodiment, as with various previously described embodiments, the delivery catheter 120 and the funnel 106" are connected or engaged as in FIG. 12A and step 402 and, as in FIG. 12B and step 404, the prosthetic heart valve device 150 is attached using, e.g., a pull wire threaded through the lumen of the delivery catheter 120 and adapted to hold the expanded prosthetic heart valve device 150 in position within the funnel 106" as well as to provide a distal force that forces the collapsing of the prosthetic heart valve device 150 into the lumen of the funnel's cylindrical or conical portion and, ultimately, into the lumen of the delivery catheter 120.

Figure 10:
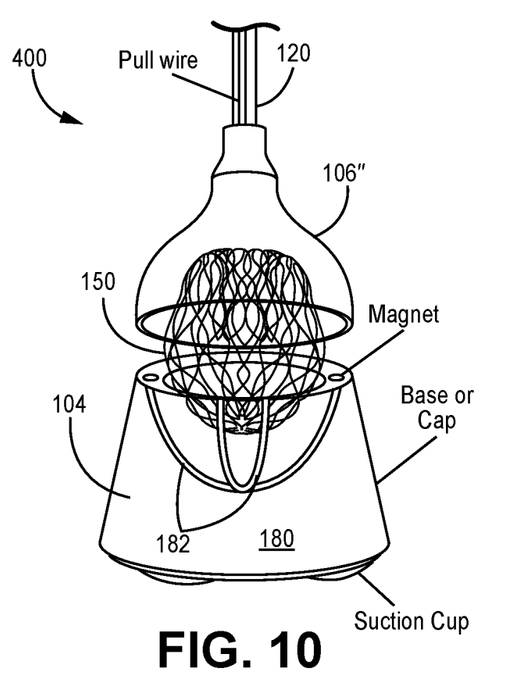
FIG. 10 illustrates a perspective view of one embodiment of the present invention.
Figure 11:
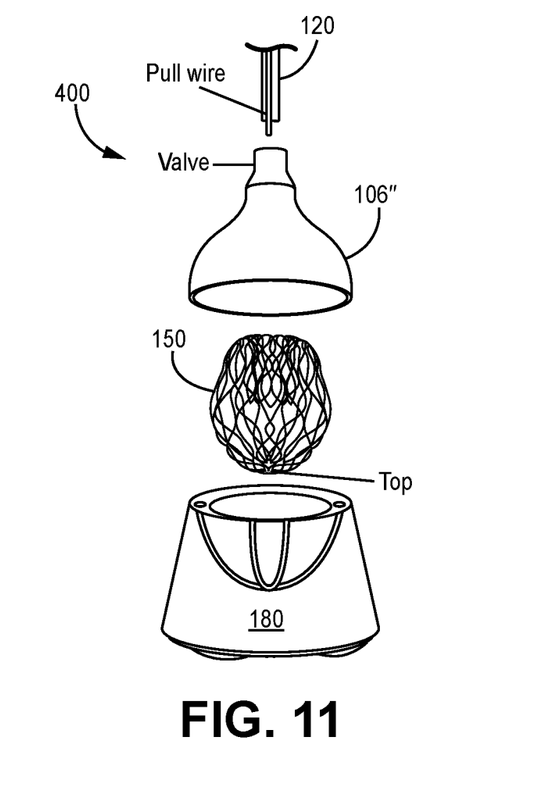
FIG. 11 illustrates an exploded view of one embodiment of the present invention.
Figure 12C:
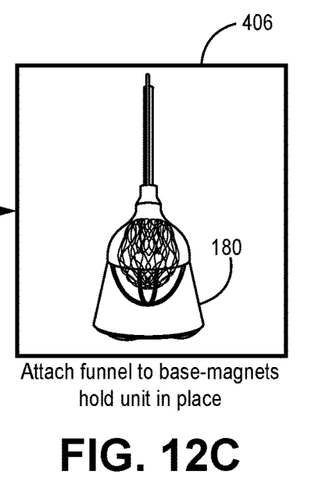
FIG. 12C illustrates an exemplary method step for loading a collapsible prosthetic heart valve device into the lumen of a delivery catheter according to embodiments of the present invention.

As shown in FIG. 12C and step 406, once the expanded prosthetic heart valve device 150 is positioned in the funnel 106" the funnel may be attached magnetically to a base or cap 180 comprising an interior sized, shaped and adapted to receive at least a portion of the expanded prosthetic device 150 therein. As also shown in FIG. 10, the top portion of the expanded device 150 is disposed within the base or cap 180. Moreover, a series of ribs or supports 182 may be provided within base or cap 180 to support the expanded device, wherein the ribs or supports 182 are at least partially immersed in biocompatible fluid. In other embodiments, the ribs may be omitted. The cylindrical or conical portion of the funnel, as in all prior embodiments discussed herein, may comprise a valve to prevent air and/or fluid moving into the lumen of the delivery catheter 120.

Figure 12D:
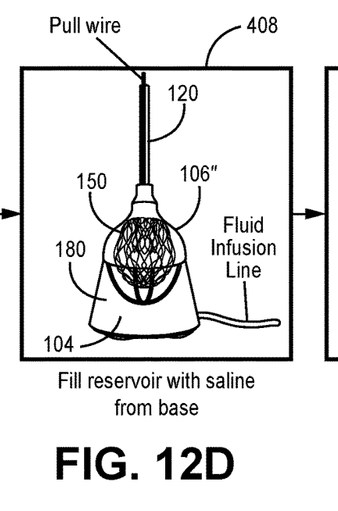
FIG. 12D illustrates an exemplary method step for loading a collapsible prosthetic heart valve device into the lumen of a delivery catheter according to embodiments of the present invention.
Figure 12E:
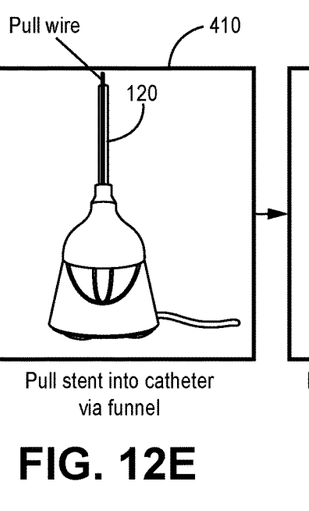
FIG. 12E illustrates an exemplary method step for loading a collapsible prosthetic heart valve device into the lumen of a delivery catheter according to embodiments of the present invention.

Turning to FIG. 12D and step 408, once the funnel 106" and the base or cap 180 are magnetically coupled together a substantially watertight sealed interior is defined and created thereby. A fluid infusion line may be in fluid communication with the base or cap 180, or with the funnel, to provide controlled infusion of biocompatible fluid into the watertight sealed interior and to fully, or at least partially, immerse the expanded device 150, or the base or cap 180 may simply be manually filled with fluid 104. At this point, as in FIG. 12E and step 410, the collapsing of the prosthetic heart valve device 150 may be initiated by pulling distally on the pull wire, collapsing the device 150 as described above and including in some cases the inner valve support, into the funnel lumen and ultimately into the lumen of the delivery catheter 120, past the valve of the funnel lumen (when present).

Figure 12F:
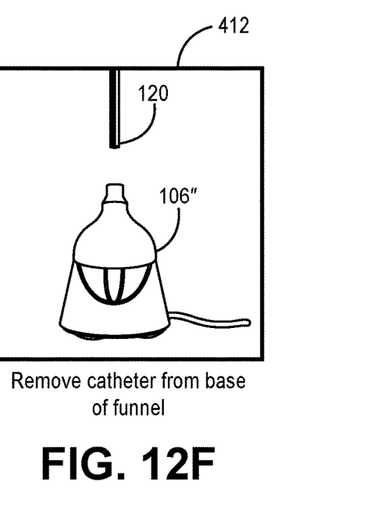
FIG. 12F illustrates an exemplary method step for loading a collapsible prosthetic heart valve device into the lumen of a delivery catheter according to embodiments of the present invention.

When the collapsed prosthetic heart valve device 150 is at a predetermined position within the lumen of the delivery catheter 120 is "loaded" therein and the catheter 120 and the funnel 106" may be disconnected. This is shown in FIG. 12F and step 412.

In all embodiments, when the collapsed prosthetic heart valve device is "loaded" within the lumen of the delivery catheter, it may be delivered via the delivery catheter through the patient's vasculature to the heart chamber of interest using any acceptable access route and/or delivery technique, including but not limited to: transapical; transfemoral; transatrial; and transseptal delivery techniques The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A loading system for an expandable and collapsible prosthetic heart valve device, comprising:
   a loading funnel adapted to hold the expanded expandable and collapsible prosthetic heart valve device therein and comprising a lumen therethrough a self-sealing access opening in the lumen;
   a connecting top adapted to connect to an upper opening of the loading funnel, thereby defining a substantially watertight interior;
   a fluid infusion line in fluid communication with the substantially watertight interior adapted to infuse biocompatible fluid into the substantially watertight interior and configured to fill the substantially watertight interior with the biocompatible fluid to immerse the prosthetic heart valve device and to eliminate air from the substantially watertight interior;
   a delivery catheter comprising a lumen in operative connection with the lumen of the loading funnel, the delivery catheter having a proximal end that is in fluid communication with the substantially watertight interior; and
   a pull wire connected with an expanded expandable and collapsible prosthetic heart valve device that is disposed within the loading funnel and extending through the lumen of the delivery catheter and extending distally beyond a distal end of the delivery catheter,
   wherein the pull wire is detachable from the prosthetic heart valve and configured to collapse and pull the expandable and collapsible prosthetic heart valve device through the lumn of the loading funnel and into the lumen of the delivery catheter,
   wherein the expandable and collapsible prosthetic heart valve device comprises an outer stent frame and an inner valve support disposed within the outer stent frame, wherein the outer stent frame surrounds the inner valve support and the loading system provides predictable and repeatable collapsing of both the outer stent frame and the inner valve support.

2. The loading system of claim 1, wherein the self-sealing access opening comprises a valve.

3. The loading system of claim 1, wherein the loading funnel and connecting top are threadingly connected together.

4. The loading system of claim 1, wherein the loading funnel is configured to ensure that loading forces are evenly distributed around the prosthetic heart valve device during collapsing and loading of the expandable and collapsible prosthetic heart valve device into the delivery catheter lumen.

* * * * *

UNITED STATES PATENT AND TRADEMARK OFFICE
CERTIFICATE OF CORRECTION

PATENT NO. : 11,452,628 B2
APPLICATION NO. : 16/848328
DATED : September 27, 2022
INVENTOR(S) : Jason S. Diedering and Saravana B. Kumar It is certified that error appears in the above-identified patent and that said Letters Patent is hereby corrected as shown below:

In the Claims

Column 9 Claim 1, Line 37, replace "therethrough a" with --therethrough and a--; Column 10 Line 13, replace "an" with --the--; Column 10 Line 21, replace "lumn" with --lumen--.

Signed and Sealed this
Twenty-third Day of May, 2023

Katherine Kelly Vidal
*Director of the United States Patent and Trademark Office*